(12) United States Patent
Romero

(10) Patent No.: US 7,074,927 B2
(45) Date of Patent: Jul. 11, 2006

(54) HETEROCYCLIC AMINES HAVING CENTRAL NERVOUS SYSTEM ACTIVITY

(75) Inventor: Arthur G. Romero, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 11/024,295

(22) Filed: Dec. 23, 2004

(65) Prior Publication Data

US 2005/0107378 A1   May 19, 2005

Related U.S. Application Data

(62) Division of application No. 10/117,634, filed on Apr. 5, 2002, which is a division of application No. 09/313,534, filed on May 13, 1999, now Pat. No. Re. 38,452.

(51) Int. Cl.
C07D 471/04 (2006.01)
(52) U.S. Cl. ....................................................... 546/84
(58) Field of Classification Search .................. 546/84
See application file for complete search history.

(56) References Cited

U.S. PATENT DOCUMENTS

| | | | |
|---|---|---|---|
| 4,110,339 A | 8/1978 | Bach et al. | |
| 5,151,431 A | 9/1992 | Inaba et al. | |
| 5,273,975 A | 12/1993 | Moon et al. | |
| RE38,452 E | 3/2004 | Romero | |

FOREIGN PATENT DOCUMENTS

| | | |
|---|---|---|
| DE | 2139107 | 2/1973 |
| DE | 3346573 | 7/1985 |
| EP | 153083 | 8/1985 |
| JP | 41-13741 | 10/1963 |
| WO | WO-87/04153 | 7/1987 |
| WO | WO-88/04292 | 6/1988 |
| WO | WO-90/15058 | 12/1990 |

OTHER PUBLICATIONS

**Evans, D.D., Peters, D. J., J. Chem. Soc., Perkin Trans. 1, pp. 285-288 (1974).
**Glennon et al. I, "2, 3—Dihydro and carboyclic, et al." CA 96:302 (1982).
**Moon et al., "Synthesis of tritium-labeled, etc." CA 118:101872 (1993).
**Kusuda et al., "N-Substituted 1, 2, 3,-4-tetrahydroquinoline, etc." CA 65:107987 (1966).
**Satoda et al., "Synthesis of quinoline derivatives, etc." CA 62:9040 (1965).
**Pohlke et al., "Heterocycle—substituted adnosines" CA 78:136628.
**Glennon et al. II, "2, 3-Dihydro and carbocyclic, etc." J. Med. Chem. 1982, 25:68-70.

*Primary Examiner*—Patricia L. Morris
(74) *Attorney, Agent, or Firm*—Marshall, Gerstein & Borun, LLP

(57) ABSTRACT

Tricyclic nitrogen containing compounds, having anxiolytic and anti-depressant activity and central nervous system activity of the following structural formula:

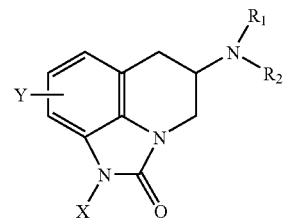

and pharmaceutically acceptable salts thereof wherein $R_1$ and $R_2$ are independently hydrogen, $C_{1-6}$ alkyl or $R_1$ and $R_2$ are joined to form pyrrolidine, piperidine, morpholine or imidazole. X is $OCH_3$, $SO_2R_3$, $SO_2CF_3$ or CN where $R_3$ is $C_{1-6}$ alkyl or an Aryl; and Y is hydrogen, Cl, Br, F, CN, $CONR_1R_2$, $CF_3$, $OCH_3$, $SO_2NR_1R_2$. These new compounds are suitable for treating anxiolytic disorder, schizophrenia, Parkinson's disease, anxiety, depression or as compounds for lowering blood pressure or treating migraine headaches in patients in need of such treatment.

1 Claim, No Drawings

HETEROCYCLIC AMINES HAVING CENTRAL NERVOUS SYSTEM ACTIVITY

The present application is a divisional of U.S. application Ser. No. 10/117,634, filed Apr. 5, 2002, which is a divisional of U.S. application Ser. No. 09/313,534, filed May 13, 1999, now U.S. RE 38,452, which is a reissue of U.S. application Ser. No. 08/592,328, filed Jan. 17, 1994, issued as U.S. Pat. No. 5,652,245 on Jul. 29, 1997, now U.S. Pat. No. RE 38,452, which is a national phase of International application No. PCT/US94/06648, International filing date 17 Jun. 1994, which was a continuation in part of U.S. patent application Ser. No. 08/097,608, filed Jul. 27, 1993, now abandoned.

BACKGROUND OF THE INVENTION

The present invention is directed toward tricyclic nitrogen containing compounds, heterocyclic amines, having anxiolytic and anti-depressant activity. These new compounds are suitable for treating central nervous system disorders including schizophrenia, Parkinson's disease, anxiety or as compounds for lowering blood pressure or treating migraines.

A series of dihydrophenalenes, tricyclic amine substituted compounds, and related compounds having central nervous system activity were described in PCT Int. Pub. No. WO87/04153 and in PCT Int. Pub. No. WO88/04292. A major difference between those compounds and the present invention is that the subject compounds have at least one nitrogen atom in the tricyclic ring structure which is shared by two of the ring structures. Generally, the subject compounds have exhibited anxiolytic activity and better oral bioavaiability.

Information Disclosure Statement

PCT Int. Pub. No. WO87/04153 and PCT Int. Pub. No. WO88/04292 each describe tricyclic structures having central nervous system activity.

U.S. Pat. No. 4,110,339 discloses 4-(di-n-propyl)amino-1,3,4,5-tetrahydrobenz(cd)indole compounds useful as prolactin inhibitors and in the treatment of Parkinsonism. European Patent Application 153,083 and German Patent 3,346,573 disclose methoxy substituted 4-(di-n-propyl)amino-1,3,4,5-tetrahydrobenz(cd)indole compounds. These publications disclose nitrogen containing tricyclic ring structures but the nitrogen is not shared by any of the rings.

Evans, D. D., Peters, D. J., *J. Chem. Soc.*, Perkin Trans. 1, pp 285–88 (1974) discloses nitrogen containing tricyclic ring structures where the nitrogen is shared by two ring structures but additionally includes other substituents not common to the subject compounds.

PCT Int. Pub. No. WO 90/15058 discloses compounds with the characteristic tricyclic nitrogen containing structure of the subject invention with the exception of the ring nitrogen "X" substituents.

SUMMARY OF THE INVENTION

In one aspect, the present invention is directed toward tricyclic nitrogen containing compounds of Formula I:

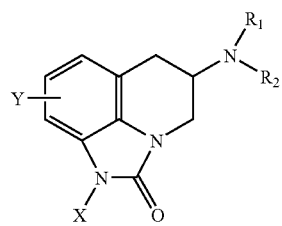

and pharmaceutically acceptable salts thereof. $R_1$ and $R_2$ are independently hydrogen, $C_{1-6}$ alkyl or $R_1$ and $R_2$ are joined to form pyrrolidine, piperidine, morpholine or imidazole. X is $OCH_3$, $SO_2R_3$, $SO_2CF_3$ or CN where $R_3$ is $C_{1-6}$ alkyl or an Aryl; and Y is hydrogen, Cl, Br, F, CN, $CONR_1R_2$, $CF_3$, $OCH_3$, $SO_2NR_1R_2$.

These new compounds have been found to exhibit anxiolytic activity in isolation induced aggression and plasma corticosterone models. They are also suitable for treating various central nervous system disorders effected by $5\text{-HT}_{1A}$ receptors such as, schizophrenia, Parkinson's disease, anxiety, depression, or as compounds for lowering blood pressure and treating migraine headaches in patients in need of such treatments.

In yet another aspect, the present invention is a method for treating central nervous system (CNS) disorders influenced by $5\text{-HT}_{1A}$ receptors such as anxiety, depression, hypertension and associated high blood pressure, Parkinson's disease and schizophrenia in animal or human hosts by administering a pharmaceutically effective amount of a compound of Formula I including pharmaceutically acceptable salts. Other uses for these compounds include panic attacks, eating disorders, obsessive-compulsive disturbances seen in dementia disorders. In addition, central 5-HT receptor activation are believed to be involved in mediating sexual behavior and therefore these compounds would be useful to stimulate sexual activity and to alleviate impotence.

DETAILED DESCRIPTION OF THE INVENTION

The present invention describes compounds of Formula I, above, having central nervous system activity. The compounds are characterized by a tricyclic ring structure having a shared nitrogen atom between two rings, an amine substituent ($NR_1R_2$) and a substituted ring nitrogen (X) as structurally depicted by Formula I. The systematic names for the ring systems in these compounds may be found by consulting the Ring Systems Handbook, 1988 edition, published by Chemical Abstracts Service. These names are derived by combining the names of benzene or a monocyclic heterocycle with the name of a bicyclic heterocycle to which it is fused. The atoms and bonds common to the fused rings are then specified to distinguish it from isomeric systems with similar names.

The particular compounds have been found to be active in various central nervous system screens such as hypothermia and hypoxic stress tests and have been found to be dopamine and serotonin such as, $5HT_{1A}$ receptor binding assay antagonists.

The following definitions are applied to the structural formula represented by Formula I, above.

"$C_1$–$C_6$ alkyl" means methyl, ethyl propyl butyl pentyl and hexyl and isomeric forms thereof.

"Aryl" means aromatic ring structures containing five to ten carbon atoms which can be optionally substituted with halogen atoms, $C_{1-6}$ alkyl (which can be optionally substituted with halogen and hydroxyl groups) and hydroxyl groups such as phenyl, α-naphthyl, β-naphthyl, m-methylphenyl p-trifluoromethylphenyl and the like. Aryl also includes the various heteroaryl groups which contain the heteroatoms nitrogen, sulfur or oxygen to form pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl and 5-isothiazolyl.

"Pharmaceutically acceptable salts" are hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and other pharmaceutically acceptable counter ions for amines. Additionally, the compounds of this invention may be administered in a suitable hydrated form.

The compounds of the invention include both racemic and optically pure products which can be separated by conventional methods into the R- and S-isomers. Resolution can be accomplished using resolving agents such as optically active dibenzoyltartaric acid, camphorsulfonic acid, bis-o-toluoyltartaric acid, tartaric acid, and diacetyl tartaric acid.

A second procedure useful in resolving primary and secondary amine compounds of Formula I involves their conversion to diastereomeric amides using an optically active acid. The diastereomeric amides are separated and the amide bond is cleaved to afford the optically pure Formula I compounds. This procedure is illustrated in PCT International Publication No. WO 90/15058 (Examples 49 and 50) for the preparation of the optical isomers using t-butoxycarbonyl-L-phenylalanine as the resolving agent. For the resolution, the racemic compound is coupled to t-butoxycarbonyl-L-phenylalanine and the diastereomeric amide products are separated by chromatography into the (+) and (−) forms. The (−) isomer is reacted with trifluoracetic acid to give (−) N-(5,6-dihydro-2-oxo-4H-imidazo(4,5,1-ij) quinolin-5-yl)-L-phenylalanineamide. Edman degradation of this compound, by reaction with phenyl isothiocyanate followed by trifluoracetic acid, removes the phenylalanine residue and affords the (−) form of the compound. Further reaction of this product with propionaldehyde and sodium cyanoborohydride gives the (−) form of the active isomer.

General procedures for preparing compounds of Formula I are shown in Schemes 1 and 2, below, and as cross-referenced and described in the Examples. Methods for preparing various intermediates for the subject compounds are described in PCT International Publication No. WO 90/15058 herein incorporated by reference.

The dosage regimen for treating patients with the compounds of this invention is selected in accordance with a variety of factors including the type, age, weight, sex, and medical condition of the patient, the severity of the psychosis, the route of administration and the particular compound employed. An ordinarily skilled physician or psychiatrist will readily determine and prescribe the effective amount of compound to prevent or arrest the progress of the condition. In so proceeding, the physician or psychiatrist could employ relatively low dosages at first, subsequently increasing the dose until a maximum response is obtained.

Initial dosages of the compounds of the invention are ordinarily in the area of at least 10 mg up to about 1200 mg per day orally, which may be given in a single dose or in multiple doses. When other forms of administration are employed equivalent doses are administered. When dosages beyond 600 mg are employed, care should be taken with each subsequent dose to monitor possible toxic effects.

The compounds of this invention are administered in oral unit dosage forms such as tablets, capsules, pills, powders, or granules. They may also be introduced parenterally, (e.g., subcutaneously, intravenously, or intramuscularly), using forms known to the pharmaceutical art. They also may be administered rectally or vaginally in such forms as suppositories or bougies. In general the preferred route of administration is oral.

The compounds of this invention can also be administered as pharmaceutically or therapeutically acceptable salt such as hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and the lie. Additionally, the compounds of this invention may be administered in a suitable hydrated forum.

Compounds of the subject invention were evaluated in an isolation-induced aggression assay to measure their ability to control or arrest aggressive behavior as measured against a saline "Control". Male CF-1 mice (Charles River Labs) were housed singly in wire cage drawers for several weeks of isolation and aggression training. After this, the isolated mouse (weighing 30–50 g) initiated an "attack" whenever an intruder mouse was placed into his cage. Intruders were male CF-1 Charles River mice, about the same size as isolated mice and housed in groups of 12 per cage. For drug testing, the isolated mice were dosed orally (p.o.) with drug or 0.25% methylceflulose vehicle. Thirty minutes later, an intruder mouse was introduced and the latency to attack was recorded. Treatment groups (n=6), including a positive control, were tested by an observer blinded to the treatments, and there was an additional non-blinded vehicle group. The results were as follows:

| Compound | Seconds |
| --- | --- |
| Control | 66 |
| Example 1[1] | 600 |
| Control | 152 |
| Example 2[2] | 565 |
| Control | 66 |
| Example 2[3] | 600 |

[1]Formula I where $R_1$ is hydrogen, $R_2$ is methyl, Y is hydrogen and X is —$OCH_3$ (R-enantiomer);
[2]Formula I where $R_1$ is methyl, $R_2$ is methyl, Y is hydrogen and X is —$OCH_3$ (racemate);
[3]Formula I where $R_1$ is methyl, $R_2$ is methyl, Y is hydrogen and X is —$OCH_3$ (R-enantiomer).

Compounds of Example 4 (Formula I where $R_1$ and $R_2$ are propyl, Y is hydrogen and X is —$OCH_3$) were evaluated in an receptor binding assay (5HT Ligand) for calculation of IC$_{50}$ values and Ki (nM) values. Receptor binding assays are well known tests for evaluating compounds for activity as described in "Cloning and Pharmacological Characterization of a Novel Human 5-hydroxy-1-tryptamine$_{1D}$ Receptor Sub-Type", Mol. Pharm., 42 439–44 (1992), herein incorporated by reference. The results were as follows:

| Compounds Ex. 4 | Receptor | Ligand | Ki (nM) |
|---|---|---|---|
| Racemate | 5-HT1DA-Clone | 5HT | 15.20 |
| " | 5-HT1DB-Clone | 5HT | 7.17 |
| R-Enantiomer | 5-HT1DA-Clone | 5HT | 38.00 |
| " | 5-HT1DB-Clone | 5HT | 58.00 |
| " | 5-HT1A-Clone | DPAT | 97 |
| S-Enantiomer | 5-HT1A-Clone | DPAT | 904 |

The above data shows that the racemate compound is selective for the 5HT$_{1DB}$ receptor and that the activity resides in the R-enantiomer compound.

EXAMPLE 1

(R)-5-Methylamino-1-methoxy-5,6-dihydro-4H-imidazo[4,5,1-ij]-quinolin-2(1H)-one (8a)

Preparation of Methyl (R)-N-(1,2,3,4-tetrahydro-1-methoxy-2-oxo-3-quinolinyl)carbamate (2a)

A solution of methyl chloroformate (42.8 g, 0.453 mol) in chloroform (50 ml) was added to a mixture of (R)-1,2,3,4-tetrahydro-1-methoxy-2-oxo-3-quinolinamine 1 (M. Kawase, T. Kitamura, Y. Kilugawa, J. Org. Chem., 54, 1989 3394–3403)(0.15 mol) and sodium bicarbonate (50.4 g, 0.600 mol) in chloroform (250 ml) and water (100 ml) over a period of 10 minutes at 0° C. The mixture was stirred overnight at room temperature, diluted with pentane, and the layers were separated. The aqueous layer was extracted with diethylether, and the combined organic extracts were washed with brine and dried (MgSO$_4$). The solvent was removed under vacuum to leave an amber oil. Purification by flash chromatography (230–400 mesh silica gel, 35–40% ethyl acetate in hexane) gave the title compound as a light yellow oil (37.0 g, 99%).

NMR (CDCl$_3$, TMS) δ2.865 (t, j=14.7 Hz, 1H), 3.437 (dd, j=6.0 & 15.3 Hz, 1H), 3.723 (s, 3H, NOCH$_3$), 3.932 (s, 3H, COOCH$_3$), 4.426 (dt, J=5.& & 14.2 Hz, 1H, N—CH), 5.856 (br. s, 1H, NH), 7.098 (t of d, j=1.2 & 7.4 Hz, 1H), 7.228 (m, 2H), 7.331 (t, j=7.7 Hz, 1H).

[α]$_D$=−47° (25° C., CHCl$_3$, c=0.9977).

Preparation of (R)-3-Methylamino-1,2,3,4-tetrahydroquinoline (3a)

A solution of (R)-N-(1,2,3,4-tetrahydro-1-methoxy-2-oxo-3-quinolinyl)carbamate (2a, 36.25 g, 0.145 mol) in tetrahydrofuran (400 ml) was cooled in ice, and borane dimethylsulfide complex (10M, 73 ml, 0.73 mol) was added. The ice bath was removed, and mixture slowly came to a vigorous reflux which required cooling with an ice bath. When the reaction subsided, it was heated at reflux on the steam bath overnight. The mixture was cooled in ice, and water (80 ml) and then 10% aqueous hydrochloric acid (70 ml) were added dropwise. The mixture (acidic by pH paper) was stirred at reflux on the steambath for 1.25 hr. The mixture was cooled in ice and basified slowly with solid sodium hydroxide. The mixture was diluted with water and pentane, and the layers were separated. The aqueous was extracted with diethylether, and the combined organic extracts were dried (MgSO$_4$). The solvent was removed under vacuum to leave an oil (23.96 g, 100%). A sample (1.3 g) was purified via gravity chromatography (70–230 mesh silica gel; 6% methanol 0.6% ammonium hydroxide, chloroform) to give the title compound as a light yellow oil (0.84 g).

NMR (CDCl$_3$, TMS) δ1.529 (br. s, 1H, methylamine NH), 2.503 (s, 3H, N—CH$_3$), 2.62–2.71 (m, 1H), 2.93–3.14 (m, 3H), 3.394 (d of t, j=2.2 & 10.9 Hz, 1H), 3.814 (br. s, 1H, NH), 6.483 (d, j=7.7 Hz, 1H), 6.624 (d of t, j=1.0 & 7.4 Hz, 1H), 6.95–6.98 (m, 2H).

The compound (0.83 g, 5.12 mmol) was dissolved in methanol and combined with a solution of trimethylsilyl chloride (0.54 g, 5.0 mmol) in methanol, and the solvent was removed under vacuum. The residue was crystallized from methanol/diethylether to give the hydrochloride salt of the title compound (3a) as light yellow-green crystals (0.56 g, m.p. 193–195° C.).

[α]$_D$=+26° (25° C., CH$_3$OH, c=1.0232).

Preparation of (R)-N-Methyl-N-[3-((1-trifluormethylacetyl)-1,2,3,4-tetrahydroquinolinyl)]trifluoromethylacetamide (4a)

A solution of (R)-3-Methylamino-1,2,3,4-tetrahydroquinoline (3 a, 21.32 g, 0.131 mol) in tetrahydrofuran (200 ml) was cooled in ice, and trifluoroacetic anhydride (69.2 g, 0.329 mol) was added dropwise. The mixture was stirred at 0° C. for 1 hr and at room temperature for 2 hr. The mixture was again cooled in ice and water (150 ml) was added. Solid sodium bicarbonate was added portionwise until the evolution of gas ceased. The mixture was extracted three times with diethylether, and the combined organic extracts were washed with saturated sodium bicarbonate and brine. The solution was dried (MgSO$_4$), and the solvent was removed under vacuum to leave a yellow oil (42.2 g). Purification by flash chromatography (230–400 mesh silica gel; 15% ethyl acetate in hexane) gave the title compound as a yellow oil (31.12 g, 67% yield).

[α]$_D$=+59° (25° C., CHCl$_3$, c=0.5495).

MR (CDCl$_3$, TMS) δ2.75–3.40 (m, 5H), 3.65–3.95 (m, 1H), 3.95–4.30 (m, 1H), 4.572 (quintet, j=7.6 Hz, 0.3H), 4.921 (m, 0.7H), 7.15–7.45 (m, 3.7H), 7.697 (m, 0.3H).

Preparation of (R)-3-Methylamino-1-trifluoromethylacetyl-1,2,3,4-tetrahydroquinoline (5a)

A solution of (R)-N-Methyl-N-[3-((1-trifluormethylacetyl)-1,2,3,4-tetrahydroquinolinyl)]trifluoromethylacetamide (4a, 29.78 g, 84.1 mmol) in tetrahydrofuran (140 ml) was cooled in ice and a solution of potassium hydroxide (45.6% solution, 7.5 ml, 89.3 mmol) in water (40 ml) was added. The mixture was stirred a 0° C. for 30 minutes and at room temperature for 1 hour. The mixture was extracted twice with diethylether. The combined organic extracts were washed with brine and dried (MgSO$_4$). The solvent was removed under vacuum to leave a yellow oil (21.7 g, 100%). A sample (1.05 g) was purified via flash chromatography (230–400 mesh silica gel, 15% ethyl acetate in hexane) gave a yellow oil (0.90 g). Crystallization from ethyl acetate/hexane gave the title compound as a colorless solid (0.45 g, m.p. 68–69° C.).

NMR (CDCl$_3$, TMS) δ2.871–3.182 (m, 5H, N—CH$_3$ & Ar—CH$_2$), 3.33–3.449 (m, 2H, N—CH$_2$), 3.890 (br. s, 1H,

NH), 4.35–4.48 (m, 0.4H, N—CH), 4.800–4.888 (m, 0.6H, N—CH), 6.553 (t, j=7.6 Hz, 1H), 6.660–6.735 (m, 1H), 6.996–7.068 (m, 2H).

$[\alpha]_D$=−29° (25° C., CHCl$_3$, c=0.9917).

Preparation of (R)-N-Methyl-N-[3-(1-(N-methoxyaminocarbonyl)-1,2,3,4-tetrahydroquinolinyl)] trifluoromethylacetamide (6a)

A solution of phosgene (1.93M in toluene, 15.6 ml, 30.1 mmol) in dry tetrahydrofuran (75 ml) was cooled in ice and a solution of (R)-3-Methylamino-1-trifluoromethylacetyl-1,2,3,4-tetrahydroquinoline (5a, 7.75 g, 30.0 mmol) and triethylamine (4.20 ml, 30.1 mmol) in dry tetrahydrofuran (75 ml) was added dropwise. The mixture was stirred in an ice bath for 50 minutes, and methoxylamine hydrochloride (5.01 g, 60.0 mmol) and triethylamine (8.40 ml, 60 mmol) were added. The mixture was stirred at room temperature for 24 hours, diluted with diethylether, and washed with water, 10% hydrochloric acid, saturated sodium bicarbonate solution, and brine. The solution was dried (MgSO$_4$), and the solvent was removed under vacuum to leave a oil (8.85 g). Purification by flash chromatography (230–400 mesh silica gel, 50% ethyl acetate in hexane) gave the title compound as a colorless oil (7.42 g, 75% yield).

NMR (CDCl$_3$, TMS) δ2.817–3.097 (m, 5H, N—CH$_3$ & Ar—CH$_2$), 3.66–4.035 (m, 5H, N—CH$_2$ & O—CH$_3$), 4.38–4.863 (m, 1H, N—CH), 7.148–7.366 (m, 4H), 7.813 & 7.829 (two s, 1H, NH).

$[\alpha]_D$=+5° (25° C., CHCl$_3$, c=1.137).

Preparation of (R)-5-N-(N-Methyltrifluoromethylacetamido)-1-methoxy-5,6-dihydro-4H-imidazo[4,5,1-ij]quinolin-2(1H)-one (7a)

A solution of (R)-N-Methyl-N-[3-(1-(N-methoxyaminocarbonyl)-1,2,3,4-tetrahydroquinolinyl)]trifluoromethylacetamide (6a, 6.61 g, 20.0 mmol) in chloroform (100 ml) was degassed with argon and bis(trifluoroacetoxy)iodobenzene (10.32 g, 24 mmol) was added portionwise. The solution was stirred at reflux for 7 minutes. The reaction mixture was cooled, diluted with pentane, and washed twice with saturated sodium bicarbonate solution and once with brine. The solution was dried (MgSO$_4$), and the solvent was removed under vacuum to leave a red-brown oil (11.5 g). Purification by flash chromatography (230–400 mesh silica gel; 35–40% ethyl acetate in hexane) gave an amber solid (4.74 g, 72% yield). Crystallization from ethyl acetate/hexane gave the title compound as off-white crystals (4.55 g, m.p. 148.5–150.5° C.).

NMR (CDCl$_3$, TMS) δ2.995–3.299 (m, 5H, N—CH$_3$ & Ar—CH$_2$), 3.724–3.839 (m, 1H), 4.089 & 4.099 (two s, 3H, O—CH$_3$), 5.059–4.227 (m, 1H), 4.520 (heptet, j=5.4 Hz, 0.3H), 4.931 (heptet, j=5.1 Hz, 0.7H), 6.900–7.121 (m, 3H).

$[\alpha]_D$=+38° (25° C., CHCl$_3$, c=1.0215).

Preparation of (R)-5-Methylamino-1-methoxy-5,6-dihydro-4H-imidazo[4,5,1-ij] quinolin-2(1H)-one (8a)

Potassium carbonate (2.05 g, 14.8 mmol) was added to a solution of (R)-5-N-(N-methyltrifluoromethylacetamido)-1-methoxy-5,6-dihydro-4H-imidazo[4,5,1-ij]quinolin-2(1H)-one (7a, 3.75 g, 11.4 mmol) in methanol (75 ml). The mixture was stirred at reflux for 7 hours. The solvent was removed under vacuum, and the residue was partitioned between diethylether and water(0.75 ml). The aqueous solution was saturated with brine and extracted twice more with diethylether. The combined organic extracts were dried (MgSO$_4$), and the solvent was removed under vacuum to leave an oil. After standing for three days, the aqueous developed a precipitate which was extracted twice with 75% tetrahydrofuran in diethylether. The combined organic extracts were dried (MgSO$_4$), and the solvent was removed under vacuum to leave a brown semisolid. The combined samples were purified via flash chromatography (230–400 mesh silica gel, 70–80% tetrahydrofuran in ethyl acetate to give the title compound as an amber oil (2.7 g, 100%).

NMR (CDCl$_3$, TMS) δ2.545 (s, 3H, N—CH$_3$), 2.781 (dd, j=7.4 & 16.1 Hz, 1H), 3.071 (dd, j=4.0 & 16.0 Hz, 1H), 3.233 (heptet, j=3.8 Hz, 1H), 3.645 (dd, 7.0 & 12.4 Hz, 1H), 4.045 (m, 1H), 4.088 (s, 3H, NOCH$_3$), 6.893 (d, j=7.4 Hz, 1H), 6.964 (d, j=7.1 Hz, 1H), 7.039 (t, j=7.7 Hz, 1H).

A sample (0.70 g) was dissolved in tetrahydrofuran, diluted with diethyl ether, and excess ethereal hydrochloric acid was added. The precipitate was filtered, washed with diethylether, and crystallized from methanol/diethylether to give the hydrochloride salt of the title compound (8a) as tan crystals (0.68 g, m.p. 196–197° C.).

$[\alpha]_D$=−26° (25° C., CH$_3$OH, c=1.0139).

EXAMPLE 2

(R)-5-Dimethylamino-1-methoxy-5,6-dihydro-4H-imidazo[4,5,1-ij]quinolin-2(1H)-one (9a)

Following the procedure of Example 1, a solution of (R)-5-Methylamino-1-methoxy-5,6-dihydro-4H-imidazo[4,5,1-ij]quinolin-2(1H)-one (8a, 1.88 g, 8.06 mmol) in methanol (40 ml) was stirred at room temperature, and 37% aqueous formaldehyde (2.40 ml, 32 mmol) and acetic acid (0.98 g, 16.2 mmol) were added. The mixture was cooled in ice, and sodium cyanoborohydride (1.15 g, 17.0 mmol) was added portionwise over a 5 minute period. The mixture was stirred at 0° C. for 5 minutes and at room temperature for 6 hours. The solvent was removed under vacuum, and the residue was diluted with 10% sodium carbonate solution and extracted twice with diethylether. The combined organic extracts were washed with brine and dried (MgSO$_4$). The solvent was removed under vacuum to leave an amber oil (2.06 g). Purification by flash chromatography (230–400 mesh silica gel, 65% tetrahydrofuran in ethyl acetate) gave the title compound as an amber oil (1.77 g, 89% yield).

NMR (CDCl$_3$, TMS) δ2.436 (s, 6H, N—CH$_3$), 2.853–3.068 (m, 3H), 3.525–3.596 (m, 1H), 4.081 (s, 3H, O—CH$_3$), 4.188–4.243 (m, 1H), 6.890 (d, j=7.4 Hz, 1H), 6.954 (d, j=7.1 Hz, 1H), 7.033 (t, j=7.6 Hz, 1H).

The compound was dissolved in diethylether and excess ethereal hydrochloric acid was added. The precipitate was filtered, washed with ether and crystallized from methanol/diethylether to give the hydrochloride salt of the title compound (9a) as yellow crystals (1.76 g, 195° C.).

$[\alpha]_D$=−19° (25° C., CH$_3$OH, c=1.0234).

EXAMPLE 3

(R)-5-Propylamino-1-methoxy-5,6-dihydro-4H-imidazo[4,5,1-ij]quinolin-2(1H)-one (8b)

(R)-N-(1,2,3,4-Tetrahydro-1-methoxy-2-oxo-3-quinolinyl)propanamide (2b)

The amine (1, 33.51 g, 0.135 mol) was dissolved in propionic anhydride (78.2 g, 0.60 mol) while controlling the temperature with an ice bath. The mixture was stirred at room temperature for 5 hours, and water (100 ml) was added, saturated NaHCO$_3$ (200 ml) was slowly added, and then 10% Na$_2$CO$_3$ was slowly added to neutralize the mixture to pH 7.5. The mixture was extracted with diethylether, saturated with sodium chloride, and extracted again with diethylether and a mixture of diethylether and chloroform. The combined extracts were washed with 5% $Na_2CO_3$ and brine. The solution was dried ($MgSO_4$), and the solvent was removed under vacuum to leave an amber oil. Purification by flash chromatography (230–400 mesh silica gel, 60% ethyl acetate in hexane) gave an oil. A sample was crystallized from ethyl acetate/hexane to give the title compound (2b) as colorless crystals (m.p. 98°–99° C.).

$[\alpha]_D = -100°$ (25° C., $CHCl_3$, c=0.9698).

NMR ($CDCl_3$, TMS) δ1.206 (t, J=7.6 Hz, 3H, CO—C—$CH_3$), 2.343 (q, J=7.6 Hz, 2H, $COCH_2$), 2.768 (t, J=14.7 Hz, 1H), 3.527 (dd, J=6.1 & 15.1 Hz, 1H), 3.934 (s, 3H, O—$CH_3$), 4.614 (d of t, J=5.6 & 14.2 Hz, 1H, N—CH), 6.633 br. d, J=4.5 Hz, 1H, NH), 7.099 (d of t, J=1.2 & 7.4 Hz, 1H), 7.230 (d, J=7.9 Hz, 2H), 7.327 (t, J=7.7 Hz, 1H).

Preparation of
(R)-1,2,3,4-Tetrahydro-N-propyl-3-quinolinamine monohydrochloride (3b)

Borane methyl sulfide (10M, 42.5 ml, 0.425 mol) was added to a solution of (R)-N-(1,2,3,4-Tetrahydro-1-methoxy-2-oxo-3-quinolinyl)propanamide (2b, 21.29 g, 85.7 mmol) in tetrahydrofuran (250 ml) with stirring at room temperature. The reaction was exothermic, and an ice bath was used to control the reaction. The mixture was stirred at 0° C. for 30 minutes, at room temperature overnight, and then at reflux for 4 hours. The mixture was cooled in ice, and water (50 ml) was carefully added dropwise. When the addition was complete, 10% HCl was added dropwise until the mixture was acidic by pH paper. The mixture was stirred at room temperature for 1 hour and at reflux for 1 hour. The mixture was washed with pentane and filtered. The filtrate was basified with 15% sodium hydroxide and extracted with diethylether. The aqueous layer was saturated with sodium chloride and extracted twice with diethylether. The combined ether extracts were dried ($MgSO_4$), and the solvent was removed under vacuum to leave an oil (14.8 g, 91%). A sample (1.0 g) was purified via gravity chromatography (70–230 mesh silica gel, 90 g; 3% methanol 0.3% $NH_4OH$, $CHCl_3$) to give the title compound as a colorless oil.

NMR ($CDCl_3$, TMS) δ0.924 (t, J=7.4 Hz, 3H, $CH_3$), 1.518 (sextet, J=7.4 Hz, 3H), 2.641–2.711 (m, 3H), 2.965 (dd, J=4.0 & 14.7 Hz, 1H), 3.048–3.131 (m, 2H), 3.361–3.432 (m, 1H), 3.825 (br. s, 1H), 6.488 (d, J=7.9 Hz, 1H), 6.626 (d of t, J=1.0 & 7.4 Hz, 1H), 6.951–7.002 (m, 2H).

The compound (0.85 g, 4.47 mmol) was combined with a solution of trimethylsilyl chloride (0.57 ml 4.49 mmol) in methanol. The solvent was removed under vacuum to leave a solid, which was crystallized twice from methanol/diethylether to give the hydrochloride salt of the title compound (3b) as off-white crystals (m.p. 185–192° C.).

$[\alpha]_D = +12°$ ($CH_3OH$, 25° C., c=0.8073).

NMR ($CD_3OD$, TMS) δ1.038 (t, J=7.4 Hz, 3H, $CH_3$), 1.705–1.833 (m, 2H, propyl N—C—$CH_2$), 2.986 (dd, J=5.5 & 17.2 Hz, 1H), 3.065–3.120 (m, 2H, N—$CH_2$), 3.265–3.342 (m, 1H), 3.436–3.572 (m, 2H), 3.734–3.800 (m, 1H), 6.731–6.805 (m, 2H), 7.037–7.084 (m, 2H).

Preparation of (R)-N-Propyl-N-[3-((1-trifluormethylacetyl)-1,2,3,4-tetrahydroquinolinyl)]trifluoromethylacetamide (4b)

A solution of (R)-1,2,3,4-tetrahydro-N-propyl-3-quinolinamine (3b, 14.73 g, 77.4 mmol) in tetrahydrofuran (50 ml) was cooled in ice and trifluoroacetic anhydride (40.6 g, 0.193 mol) was added dropwise. When the addition was complete, the cold bath was removed, and the mixture was stirred overnight at room temperature. Water (75 ml) was added, and sodium bicarbonate was added portionwise until the mixture was basic to litmus. The mixture was extracted three times with diethylether, and the combined extracts were washed with saturated sodium bicarbonate solution and brine. The solution was dried ($MgSO_4$), and the solvent was removed under vacuum to leave an amber oil (28.4 g). A sample (0.87 g) was purified via flash chromatography (230–400 mesh silica gel, 5–6% ethyl acetate in hexane) to give a colorless oil which was crystallized from hexane to give the title compound (4b) as colorless crystals (0.61 g, m.p. 77–79° C.).

NMR ($CDCl_3$, TMS) δ0.897–0.985 (m, 3H, propyl $CH_3$), 1.706 (sextet, j=7.7 Hz, 2H, propyl N—C—CH2), 2.85–3.69 (m, 4H), 3.69–4.38 (m, 2.6H), 4.500 (quintet, 0.4H), 7.15–7.40 (m, 3.6H), 7.726 (br. s, 0.4H).

$[\alpha]_D = +8°$ (25° C., $CHCl_3$, c=1.0067).

Preparation of (R)-N-Propyl-N-[3-(1,2,3,4-tetrahydroquinolinyl)]trifluoromethylacetamide (5b)

A solution of N-Propyl-N-[3-((1-trifluormethylacetyl)-1,2,3,4-tetrahydroquinolinyl)]trifluoromethylacetamide (4b, 27.64 g, 72.3 mmol) in tetrahydrofuran (200 ml) was cooled in ice, and a solution of potassium hydroxide (45.6% in water, 6.07 ml, 72.3 mmol) was added. The mixture was stirred at 0° C. for 15 minutes and at room temperature for 30 minutes. The mixture was diluted with diethylether, and the layers were separated. The aqueous layer was extracted with diethylether, and the combined organic extracts were washed with brine and dried ($MgSO_4$). The solvent was removed under vacuum to leave an oil (21.4 g). Purification by flash chromatography (230–400 mesh silica gel; 10% ethyl acetate in hexane) gave a yellow oil (16.68 g, 81% yield). A sample (0.75 g) was rechromatographed using the same conditions to give an oil which crystallized (0.66 g). Crystallization from hexane gave the title compound (5b) as colorless crystals (0.54 g; m.p. 68–69° C.).

NMR ($CDCl_3$, TMS) δ0.883–0.946 (m, 3H, propyl $CH_3$), 1.58–1.77 (m, 2H, propyl N—C—$CH_2$), 2.83–2.95 (m, 1H), 3.104–3.483 (m, 4.5H), 3.708 (t, j=10.4 Hz, 0.5H), 3.893 (br. s, NH), 4.16–4.28 & 4.32–4.46 (m, 1H, N—CH), 6.546 (t, j=6.9 Hz, 1H), 6.647–6.725 (m, 1H), 6.965–7.063 (m, 2H).

$[\alpha]_D = -62°$ (25° C., $CH_3OH$, c=0.9991).

Preparation of (R)-N-Propyl-N-[3-(1-(N-methoxyaminocarbonyl)-1,2,3,4-tetrahydroquinolinyl)] trifluoromethylacetamide (6b)

A solution of phosgene (1.93 M in toluene, 10.4 ml, 20.0 mmol) in dry tetrahydrofuran (50 ml) was cooled in ice and a solution of N-Propyl-N-[3-(1,2,3,4-tetrahydroquinolinyl)] trifluoromethylacetamide (5b, 5.73 g, 20.0 mmol) and triethylamine (2.03 g, 20.1 mmol) in dry tetrahydrofuran (50 ml) was added over 5 minutes. The mixture was stirred in ice for 30 minutes, and methoxylamine hydrochloride (3.34 g, 40.0 mmol) and triethylamine (4.06 g, 40.2 mmol) were added. The mixture was stirred at room temperature for 24 hours, diluted with diethylether and washed with water, twice with 10% hydrochloric acid solution, saturated sodium bicarbonate solution and brine. The solution was dried ($MgSO_4$), and the solvent was removed under vacuum to leave an oil (7.88 g). Purification by flash chromatography (230–400 mesh silica gel; 40% ethyl acetate in hexane) gave the title compound (6b) as an oil (6.25 g).

NMR (CDCl$_3$, TMS) δ0.899–0.969 (m, 3H, propyl CH$_3$), 1.62–1.83 (m, 2H, propyl N—C—CH$_2$), 2.849–3.074 (m, 4H), 3.774 (s, 3, O—CH$_3$). 3.623–3.880 (m, 1.5H), 4.089–4.154 (m, 0.5H), 4.303–4.398 (m, 1H), 7.121–7.382 (m, 4H), 7.794 & 7.858 (two s, 1H, NH).

[α]$_D$=−29° (25° C., CHCl$_3$, c=1.0139).

Preparation of (R)-5-N-(N-Propyltrifluoromethylacetamido)-1-methoxy-5,6-dihydro-4H-imidazo[4,5,1-ij]quinolin-2(1H)-one (7b)

A solution of (R)-N-Propyl-N-[3-(1-(N-methoxyaminocarbonyl)-1,2,3,4-tetrahydroquinolinyl)]trifluoromethylacetamide (6b, 5.92 g, 16.5 mmol) in chloroform (80 ml) was degassed with argon and heated to hear reflux on the steam bath. Bis(trifluoroacetoxy)iodobenzene (8.50 g, 19.8 mmol was added portionwise. The reaction was exothermic. After the addition was complete, the solution was stirred at reflux for 5 minutes. The reaction mixture was cooled, diluted with pentane, and washed twice with saturated sodium bicarbonate solution and once with brine. The solution was dried (MgSO$_4$), and the solvent was removed under vacuum to leave an oil (9.2 g). Purification by flash chromatography (230–400 mesh silica gel; 30% ethyl acetate in hexane) gave the title compound (7b) as an amber oil (3.75 g, 61% yield).

NMR (CDCl$_3$, TMS) δ0.918–0.967 (m, 3H, propyl CH$_3$), 1.60–1.87 (m, 2H, propyl N—C—CH$_2$), 2.91–3.08 (m, 1H), 3.16–3.42 (m, 2H), 3.63–3.79 (m, 1H), 4.089 & 4.101 (two s, 3H, O—CH$_3$), 3.97–4.26 (m, 2.6H), 4.42–4.56 (m, 0.4H), 6.884–7.097 (m, 4H).

Preparation of (R)-5-Propylamino-1-methoxy-5,6-dihydro-4H-imidazo[4,5,1-ij]quinolin-2(1H)-one (8b)

A solution of (R)-5-N-(N-Propyltrifluoromethylacetamido)-1-methoxy-5,6-dihydro-4H-imidazo[4,5,1-ij]quinolin-2(1H)-one (7b, 3.50 g, 9.79 mmol) in methanol (30 ml) and water (5 ml) was cooled in ice and potassium hydroxide (45.6% in water, 1.0 ml, 11.9 mmol) was added. The mixture was stirred at 0° C. for 1 hour and at room temperature for 18 hours. The solvent was concentrated under vacuum, and the residue was partitioned between water and diethylether. The aqueous layer was saturated with sodium chloride and extracted again with diethylether. The combined organic extract was dried (MgSO$_4$), and the solvent was removed under vacuum to leave an oil (2.43 g). Purification by flash chromatography (230–400 mesh silica gel; ethyl acetate to 20% tetrahydrofuran in ethyl acetate) gave the title compound (8b) as a solid (1.79 g, 69% yield).

NMR (CDCl$_3$, TMS) δ0.927 (t, j=7.4 Hz, 3H, propyl CH$_3$), 1.112 (br. s, 1H, NH), 1.507 (sextet, j=7.3 Hz, 2H, propy N—C—CH$_2$), 2.629–2.804 (m, 3H), 3.062 (dd, j=4.2 & 16.0 Hz, 1H), 3.291 (heptet, j=4.0 Hz, 1H, N—CH), 3.557 (dd, j=7.7 & 12.2 Hz, 1H), 4.066–4.156 (m, 1H), 4.088 (s, 3H, O—CH$_3$), 6.887 (d, j=7.4 Hz, 1H), 6.961 (d, j=7.3 Hz, 1H), 7.036 (t, j=7.5 Hz, 1H).

A sample was dissolved in diethylether and excess ethereal hydrochloric acid was added. The precipitate was filtered, washed well with diethylether, and crystallized from methanol/diethylether to give the hydrochloride salt of the title compound (8b) as a yellow solid (m.p. 229 ° C. dec.).

[α]$_D$=−31° (25° C., CH$_3$OH, c=1.1099).

EXAMPLE 4

(R)-5-Dipropylamino-1-methoxy-5,6-dihydro-4H-imidazo[4,5,1-ij]quinolin-2(1H)-one (9b)

Following the procedure of Example 3, a mixture of (R)-5-Propylamino-1-methoxy-5,6-dihydro-4H-imidazo[4,5,1-ij]quinolin-2(1H)-one (8b, 0.93 g, 3.56 mmol), 1-iodopropane (3.05 g, 17.9 mmol), and potassium carbonate (1.97 g, 14.3 mmol) in acetonitrile (25 ml) was heated at reflux under nitrogen for 17 hours. 1-Iodopropane (3.05 g, 17.9 mmol) was again added, and the mixture was refluxed for an additional 5 hours. The solvent was removed under vacuum, and the mixture was diluted with water and extracted twice with diethylether. The organic extract was washed with brine and dried (MgSO$_4$). The solvent was removed under vacuum to leave an amber oil. Purification by flash chromatography (230–400 mesh silica gel; 10–25% ethyl acetate in hexane) gave the title compound (9b) as an amber oil (0.87 g, 90% yield).

NMR (CDCl$_3$, TMS) δ0.894 (t, j=7.3 Hz, 6H, propyl CH$_3$), 1.456 (sextet, j=7.3 Hz, 4H, propyl N—C—CH$_2$), 2.524 (m, 8 lines, 4H, propyl N—CH$_2$), 2.823–2.975 (m, 2H)3.277 (heptet, J=5.1 Hz, 1H), 3.435 (t, j=11.4 hz, 1H), 4.076 (s, 3H, O—CH$_3$), 4.168 (dd, j=4.1 & 11.5 Hz, 1H), 6.883 (d, j=7.6 Hz, 1H), 6.942 (d, j=7.5 Hz, 1H), 7.021 (t, j=7.6 Hz, 1H).

The compound was dissolved in diethylether, and excess ethereal hydrochloric acid was added. The precipitate was filtered, washed with diethylether, and crystallized from methanol/diethylether to give the hydrochloride salt of the title compound (9b) as an off-white solid (1.12 g, m.p. 175–176° C).

[α]$_D$=−13° (25° C., CH$_3$OH, c=1.0682).

EXAMPLE 5

(R)-5-Methylamino-1-methoxy-5,6-dihydro-4H-imidazo[4,5,1-ij]quinolin-2(1H)-one (8a) (Scheme 2: Alternative Method of Example 1)

Preparation of (R)-2-(Methoxycarbonylamino)-3-phenyl propanoic acid (2)

A solution of D-phenylalanine (25.00 g, 0.151 mol) and sodium hydroxide (6.05 g, 0.151 mol) in water (170 ml) and tetrahydrofuran (225 ml) was cooled to −15° C., and a solution of methyl chloroformate (18.6 g, 0.197 mol) in tetrahydrofuran (50 ml) was added dropwise. When the addition was ~half complete, a solution of sodium hydroxide (9.10 g, 0.227 mol) in water (20 ml) was also added dropwise. When the additons were complete, the mixture was stirred at room temperature for an additonal 2 hours and acidified with 10% hydrochloric acid. The acid was extracted twice with diethylether, and the extracts were washed with brine and dried (MgSO$_4$). The solvent was removed under vacuum to leave a clear oil (38.38 g).

HPLC 6.01 min (78.9%), 7.32 min (5.0%), 8.29 min (10.8%), 8.42 min (0.5%), 9.95 min (1.2%), 10.27 min (2.8%), 11.92 min (0.7%).

Preparation of (R)-N-Methoxy-2-(methoxycarbonylamino)-3-phenylpropanamide (3)

A solution of sodium carbonate (10.20 g, 96.2 mmol) in water (170 ml) was added to a solution of the acid (~0.148 mol) in methylene chloride. Methoxylamine hydrochloride (14.2 g, 0.170 mol) and 1-(3-dimethylaminopropyl)-3-ethylcarbodiimide (31.21 g, 0.163 mol) were added, and the mixture was stirred at room temperature for 22 hours. The mixture was diluted with tetrahydrofuran (to dissolve the precipitate) and the layers were seprated. The aqueous layer was extracted with 1:1 tetrahydrofuran/diethylether, and the combined organic extracts were washed with 10% hydrochloric acid solution and saturated sodium bicarbonate solution, and the solution was dried (MgSO$_4$). The solvent was removed under vacuum to leave a white solid (34.2 g). Crystallization from ethyl acetate gave colorless crystals (22.6 g, m.p. 154°–155° C.).

$[\alpha]_D$=+5° (25° C., CH$_3$OH, 1.0450).

Preparation of Methyl (R)-N-(1,2,3,4-Tetrahydro-1-methoxy-2-oxo-3-quinolinyl)carbamate (4)

A suspension of (R)-N-Methoxy-2-(methoxycarbonylamino)-3-phenylpropanamide (11.25 g, 44.6 mmol) in 1,2-dichloroethane (170 ml) was cooled in ice and trifluoroacetic acid (9.25 ml, 13.7 g, 0.120 mol) was added. Bis(trifluoroacetoxy)iodobenzene (19.78 g, 0.046 mol) was added portionwise over 10 min at 0° C., and the mixture was stirred at the same temperature for 1 hour. The mixture was washed with 10% sodium carbonate solution and dried (MgSO$_4$). The solvent was removed under vacuum to leave an amber oil (19.58 g). Purification by flash chromatography (230–400 mesh silica gel, 40–50% ethyl acetate in hexane) gave an amber oil which solidified (9.45 g, 85% yield). A sample (1.5 g) was crystallized from ethyl acetate/hexane to give white crystals (1.36 g, m.p. 117°–119° C.).

$[\alpha]_D$=+34° (25° C., CH$_3$OH, 0.9279).

Preparation of (R)-3-Methylamino-1,2,3,4-tetrahydroquinoline maleate (5)

A solution of (R)-N-(1,2,3,4-Tetrahydro-1-methoxy-2-oxo-3-quinolinyl)carbamate (7.27 g, 29.1 mmol) in dry tetrahydrofuran (100 ml) was cooled in a water bath (~10° C.), and boron dimethylsulfide complex (10.0M, 17.5 ml, 6.0 eq) was added. The mixture was stirred in the water bath for 1 hour and at room temperature for 1.5 hours. The mixture was heated at reflux on the steam bath for 30 hours, cooled in ice, and 10% hydrochloric acid (40 ml) was added dropwize. The mixture was refluxed on the steam bath for 1.5 hours, cooled in ice, and basified with 45% potassium hydroxide. The mixture was extracted twice with diethylether, and the combined extracts were washed with brine and dried (MgSO$_4$). The solvent was removed under vacuum to leave a clear oil 4.89 g. The compound (0.029 mol) was combined with maleic acid (3.38 g, 0.029 mol), and the mixture was crystallized from methanonal/diethylether to give the title compound as off-white crystals (5.77 g, 71% yield, VPC shows 5.451 min (100%)). A sample (1.0 g) was recrystallized from methanol/diethylether to give a colorless solid (m.p. 173.5°–175° C.).

Preparation of (R)-Methyl-(1,2,3,4-tetrahydro-3-quinolinyl) carbamic acid, phenylmethyl ester (6)

A solution of (R)-1,2,3,4-tetrahydro-N-methyl-3-quinolinamine (6.00 g, 31.5 mmol) and triethylamine (4.8 g, 47.4 mmol) in chloroform (200 ml) was cooled to −30° C., and a solution of benzyl chloroformate (5.68 g, 95% pure, 31.6 mmol) in chloroform (50 ml) was added dropwise. The mixture was stirred at −30° to 0° C. for 2 hours, and 10% sodium carbonate solution (100 ml) was added, the mixture was stirred at room temperature for 1 hour, diluted with pentane and diethylether, and the layers were separated. The aqueous layer was extracted with diethylether, and the combined organic extracts were washed with brine and dried (MgSO$_4$). The solvent was removed under vacuum to leave an oil (10.91 g). Purification by flash chromatography (230–400 mesh silica gel; 4:1 hexane/ethyl acetate) gave an oil (7.53 g, 81% yield). A sample (0.57 g) was crystallized from ethyl acetate/hexane to give white crystals (0.42 g, m.p. 78.5–80° C.). $[\alpha]_D$=−47° (25° C., CH$_3$OH, 0.8166).

Preparation of (R)-Methyl-[1,2,3,4-tetrahydro-1-[(methoxyamino)carbonyl]-3-quinolinyl]carbamic acid, phenylmethyl ester (7)

A solution of (R)-methyl-(1,2,3,4-tetrahydro-3-quinolinyl)carbamic acid, phenylmethyl ester (3.81 g, 12.86 mmol) and triethylamine (3.9 g, 39 mmol) in dry tetrahydrofuran (50 ml) was rapidly added with stirring to a solution of phosgene (1.93 M in toluene) in tetrahydrofuran (100 ml) at 0° C. The cold bath was removed, and the mixture was stirred for 1.25 hours. Methoxylamine (2.15 g, 25.7 mmol) and triethylamine (7.9 g, 78 mmol) were added, and the mixture was stirred at room temperature for 3 days. The mixture was diluted with diethylether and washed with water and brine. The solution was dried (MgSO$_4$), and the solvent was removed under vacuum to leave an oil (5.13 g, >100%) which was sufficiently pure for the next step. A sample (0.91 g) was purified via flash chromatography (230–400 mesh silica gel; 50% ethyl acetate/hexane) to give an oil. $[\alpha]_D$=+38° (25° C., CH$_3$OH, 0.9805). ass spec. m+ at m/z 369. Strongest peaks at m/z 43, 65, 91, 118, 130, 158, 173, 204.

Exact mass calcd. for C$_{20}$H$_{23}$N$_3$O$_4$: 369.1688. Found: 369.1682.

Preparation of Methyl-(1,2,5,6-tetrahydro-1-methoxy-2-oxo-4H-imidazo[4,5,1-ij]quinolinyl-5-yl)carbamic acid, phenylmethyl ester (8)

A solution of (R)-Methyl-[1,2,3,4-tetrahydro-1-[(methoxyamino)carbonyl]-3-quinolinyl]carbamic acid, phenylmethyl ester (7.26 g, 19.7 mmol) in chloroform (150 ml) was degassed with argon, and the mixture was cooled to −5° C. in an ice-salt bath Bis(trifluoroacetoxy)iodobenzene (10.14 g, 23.6 mmol) was added, and the mixture was stirred at −5 to 0° for 4 hours and at room temperature for 2 hours and was stored at −15° C. overnight. The mixture was washed with 10% sodium carbonate solution, and the aqueous washings were back extracted with diethylether. The combined organics were dried (MgSO$_4$), and the solvent was removed under vacuum to leave a brown oil (10.7 g). Purification by flash chromatography (230–400 mesh silica gel, 50% ethyl acetate in hexane) gave an amber oil which slowly solidified (5.67 g, 78%). A sample (0.54 g) was crystallized from ethyl acetate/hexane to give off-white crystals (0.41 g, m.p. 105–106.5° C. $[\alpha]_D$=+44° (25° C., CH$_3$OH, 0.7311).

Preparation of (R)-5,6-Dihydro-1-methoxy-5-(methylamino)-4H-imidazo[4,5,1-ij]quinolin-2-one (8a)

Selective Hydrogenation:

A mixture of methyl-(1,2,5,6-tetrahydro-1-methoxy-2-oxo-4H-imidazo[4,5,1-ij]quinolinyl-5-yl)carbamic acid phenylmethyl ester (1.48 g, 4.03 mmol) and 10% palladium on carbon (0.25 g) in absolute ethanol (100 ml) was stirred under one atmosphere of hydrogen. After taking up one equivalent of hydrogen, the mixture was filtered through celite, and the solvent was removed under vacuum to leave an oil.

Preparation of (R)-5,6-Dihydro-5-(methylamino)-4H-imidazo[4,5,1-ij]quinolin-2(1H)-one, monohydrochloride Exhaustive Hydrogenation:

A mixture of methyl-(1,2,5,6-tetrahydro-1-methoxy-2-oxo-4H-imidazo[4,5,1-ij]quinolinyl-5-yl)carbamic acid phenylmethyl ester (1.48 g, 4.03 mmol) and 20% palladium hydroxide on carbon (0.50 g) in absolute ethanol (100 ml) was shaken in a apparatus with an initial hydrogen pressure of 50 psi for 17 hours. The mixture was filtered through celite, and the solvent was removed under vacuum to leave an oil (0.86 g). The compound was dissoved in methanol and excess ethereal hydrochloric acid was added. The mixture was diluted with diethylether, and the precipitate was filtered and crystallized from methanol/diethylether to give an off-white solid (0.61 g, 63% yield, m.p. 310–311° C.). $[\alpha]_D = -30°$ (25° C., CH$_3$OH, 1.0182).

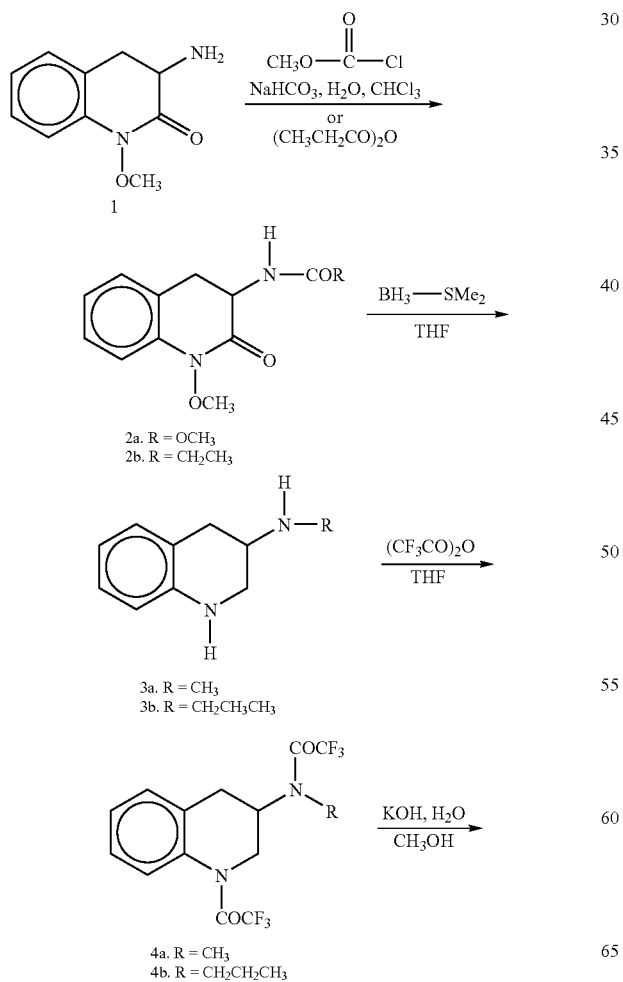

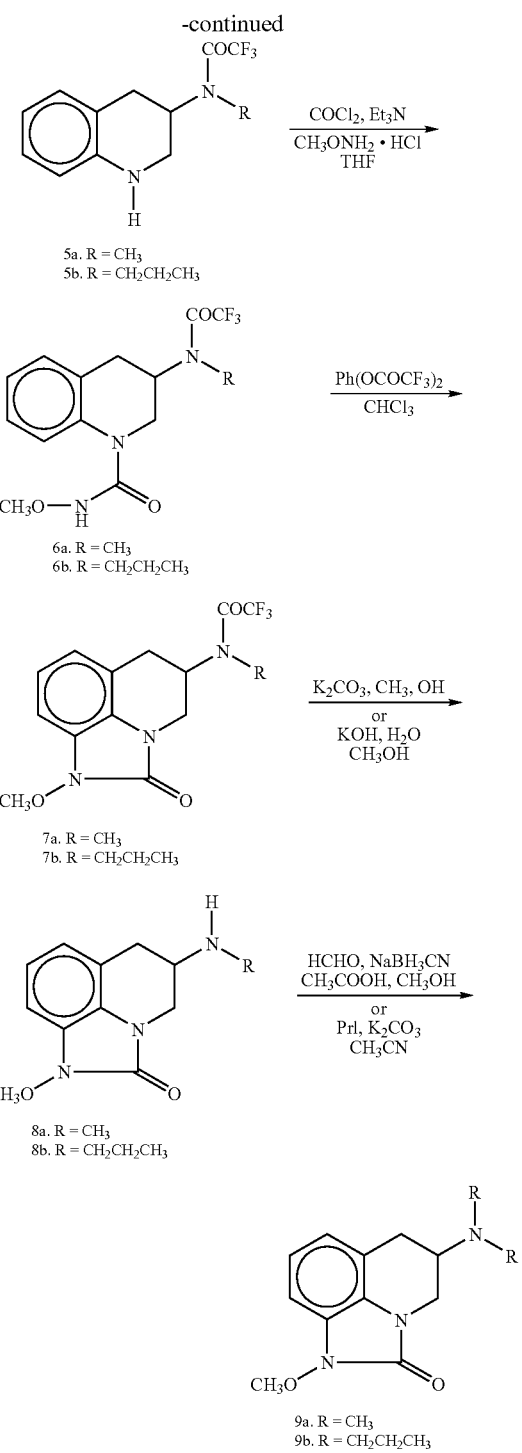

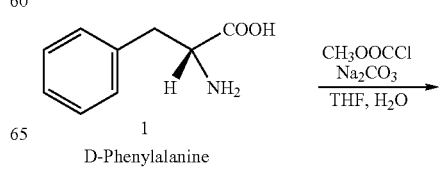

-continued
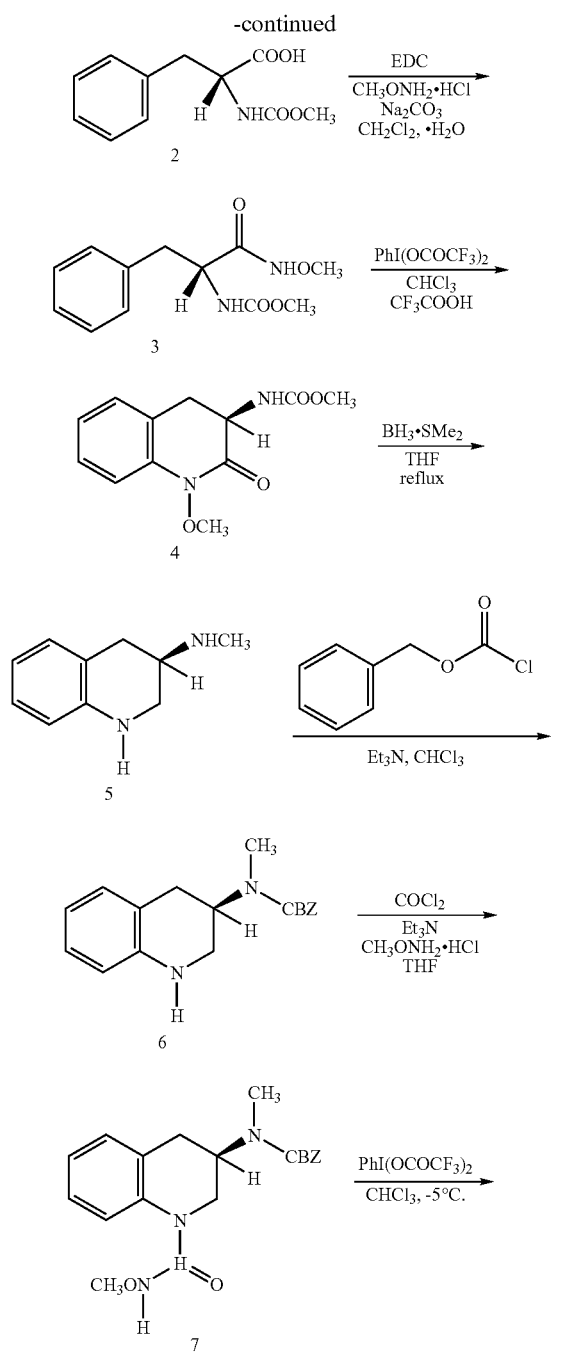
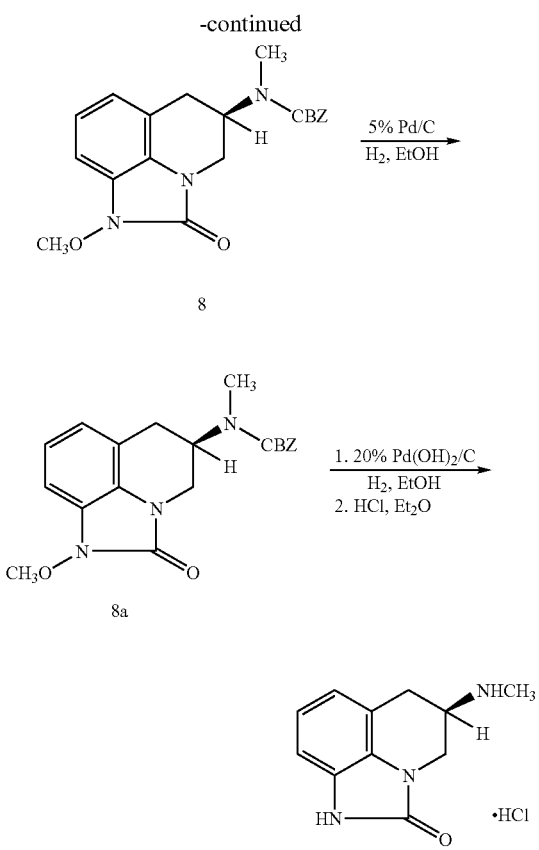
What is claimed is:
1. A compound of the following structural formula:
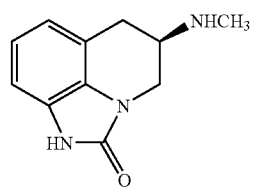
and pharmaceutically acceptable salts thereof.
* * * * *